(12) United States Patent
Borodic

(10) Patent No.: US 6,429,189 B1
(45) Date of Patent: Aug. 6, 2002

(54) CYTOTOXIN (NON-NEUROTOXIN) FOR THE TREATMENT OF HUMAN HEADACHE DISORDERS AND INFLAMMATORY DISEASES

(75) Inventor: Gary E. Borodic, Canton, MA (US)

(73) Assignee: Botulinum Toxin Research Associates, Inc., Qunicy, MA (US)

( * ) Notice: Subject to any disclaimer, the term of this patent is extended or adjusted under 35 U.S.C. 154(b) by 0 days.

(21) Appl. No.: 09/458,784

(22) Filed: Dec. 10, 1999

(51) Int. Cl.$^7$ .............................................. A01N 37/18
(52) U.S. Cl. ................................. 514/2; 514/2; 514/14; 514/825; 514/885; 424/810; 424/443; 424/430.1; 424/282.1; 530/350; 530/387.1; 530/389.5; 435/6; 435/842
(58) Field of Search .............................. 514/14, 2, 825, 514/885; 424/282.1, 810, 443, 130.1; 530/387.1, 350, 389.5

(56) References Cited

U.S. PATENT DOCUMENTS

| | | | |
|---|---|---|---|
| 5,053,005 A | 10/1991 | Borodic | 604/51 |
| 5,183,462 A | 2/1993 | Borodic | 604/51 |
| 5,298,019 A | 3/1994 | Borodic | 604/51 |
| 5,401,243 A | 3/1995 | Borodic | 604/51 |
| 5,562,907 A | 10/1996 | Arnon | 514/2 |
| 5,696,077 A | 12/1997 | Johnson et al. | 514/2 |
| 5,714,468 A | 2/1998 | Binder | 514/14 |
| 5,837,265 A | 11/1998 | Montal et al. | 424/239.1 |
| 6,063,768 A * | 5/2000 | First | 514/14 |
| 6,113,915 A | 9/2000 | Aoki et al. | 424/236.1 |

OTHER PUBLICATIONS

Ohishi et al., Infect. Immun., vol. 31, No. 3, pp.890–895, 1981.*
Acquadro M et al. Treatment of myofascial pain with botulinum A toxin. Anesthesiology 3/94;80(3): 705–6.
Amann R et al. Intraplantar injection of nerve growth factor into the rat hind paw: local edema and effects on thermal nociceptive threshold. Pain, 1995; 64: 323–329.
Ashikaga T et al. Multiple daily insulin injections in the treatment of diabetic retinopathy. The Job study revisited. Diabetes, 5/78; 27(5): 592–6.
Bischoff SC et al. Effect of Nerve Growth Factor on the Release of Inflammatory Mediators by Mature Human Basophils. Blood, May 15, 1992; 79(10): 2663–2669.
Borodic G et al. Contralateral injections of botulinum A toxin for the treatment of hemifacial spasm to achieve increased facial symmetry. Plast Reconstr Surg 12/92; 90(6): 972–7.
Borodic G Myasthenic crisis after botulinum toxin. Lancet, Dec. 5, 1998; 352(9143): 1832.
Borodic G et al. Botulinum toxin therapy, immunologic resistance, and problems with available materials. Neurology 1/96; 46(1): 26–9.

Borodic G et al. Antibodies to botulinum toxin. Neurology 1/95; 45(1): 204.
Borodic G Therapeutic botulinum toxin. Lancet Nov. 12, 1994; 344(8933): 1370.
Borodic G et al. New concepts in botulinum toxin therapy. Drug Saf 9/94; 11(3): 145–52.
Borodic G et al. Antibodies to bowline toxin. Ophthalmology 7/94; 11(3): 1158–9.
Borodic G et al. Histologic assessment of dose–related diffusion and muscle fiber response after therapeutic botulinum A toxin injection. Movement Disorders 1994; 9(1): 31–39.
Borodic G et al. Botulinum A toxin for treatment of aberrant facial nerve rgeneration. Plast Reconstr Surg 5/93; 91(6): 1042–5.
Borodic G et al. Botulinum B toxin as an alternative to botulinum A toxin: a histologic study. Ophthal Plast Reconstr Surg 1993; 9(3): 182–90.
Borodic G et al. Effects of repeated botulinum toxin injections on orbicularis oculi muscle. J Clin Neuroophthalmol 6/92; 12(2):121–7.
Borodic G et al. Botulinum A toxin for spasmodic torticollis: multiple vs single injection points per muscle. Head Neck 1–2/92; 14(1): 33–7.
Borodic G et al. Treatment of spasticity with botulinum toxin. Ann Neurol 1/92; 31(1): 113.
Borodic G Botulinum A toxin for (expressionisic) ptosis overcorrection after frontalis sling. Ophthal Plast Reconstr Surg 1992; 8(2): 137–42.
Borodic G et al. Botulinum A toxin for the treatment of adult–onset spasmodic torticollis. Plast Reconstr Surg 2/91; 87(2): 285–9.

(List continued on next page.)

Primary Examiner—Karen Cochrane Carlson
Assistant Examiner—Hope A. Robinson
(74) Attorney, Agent, or Firm—Milbank, Tweed, Hadley & McCloy LLP

(57) ABSTRACT

Pharmaceutical applications of a chemodenervating agent reduce pain by altering release of pain and inflammation-mediating autocoids, with a duration of action between 12–24 weeks. The limiting factor in dosing for this application is weakness and paralysis created by higher doses of the chemodenervating pharmaceutical. This weakness and paralysis is mediated by action of the neurotoxin component of the chemodenervating pharmaceutical. The invention described herein represents a novel mechanism and pharmaceutical formulation which eliminates the neurotoxin component of the chemodenervating pharmaceutical, while retaining the cytotoxin component which provides an essential bioeffect for the relief of pain and inflammation. The invention allows for improvement in administering the pharmaceutical agent for the reduction of pain and/or inflammation without causing muscular weakness and paralysis.

29 Claims, 2 Drawing Sheets

(2 of 2 Drawing Sheet(s) Filed in Color)

OTHER PUBLICATIONS

Borodic G et al. Innervation zone of orbicularis oculi muscles and implications fo rbotulinum A toxin therapy. Ophthal Plast Reconstr Surg 1991; 7(1): 54–60.

Borodic G et al. Botulinum A toxin for the treatment of spasmodic torticolilis dysphagia and rgional toxin spread. Head Neck 9–10/90; 12(5): 392–9.

Borodic G et al. Blepharospasm and its treatment, with emphasis on the use of botulinum toxin. Plast Reconstr Surg 3/89; 83(3): 546–54.

Borodic G et al. Dermis fat graft in eviscerated sockets. Opthal Plast Reconst Surg 1989; 5(2): 144–9.

Borodic G et al. Immunoglobulin deposition in localized conjuctival amyloidosis. Am J Ophthalmol 11/84; 98(5): 617–22.

Borodic G et al. Peripapillary subretinal neovascularization and serous macular detachment. Association with congeital optic nerve pits. Arch Opthalmol 2/84; 102(2): 229–31.

Borodic G et al. Photophobia and benign essential blepharospasm.

Borodic G et al. Therapeutic botulinum toxin; histologic effects and diffusion properties. DasGupta BR, ed. Botulinum and Tetanus Neurotoxins. Plenum Press, New York, 1993 623–45.

Borodic G. Botulinum toxin: issue and applications. Otolaryngology Head Neck Surg 1999; 219–25.

Borodic G et al. Pharmacology and histology of the therapeutic application of boulinum toxin.

Bottinger H et al. Inhibition of histamine release from rat mast cells by botulinum C2 toxin. Int Arch Allergy Appl Immunol 187; 84(4): 380–4.

Brooks A et al. Reactive oxygen species generation and histamine release by activated mast cells: modulation by nitric oxide synthase inhibition. Br J. Pharmacol 1999; 128:585–90.

Calderone J et al. Intraocular pathology of trisomy 18 (Edward's syndrome): report if a case and review of the literature. Br J Ophthalmol 3/83; 67(3): 162–9.

Chen X et al. NOS Inhibitor antagonism of PGE2–induced mechanical sensitization of cutaneous C–fiber nociceptors in the rat. Am Psych Soc 1999; 963–6.

Dines K et al. Mast cell interactions with the nervous system: relationship to mechanisms of disease. J Neuropathol Exp Neurol 1997; 56(6): 627–40.

Fujishima H et al. Elevated levels of substance P in tears of patients with allergic conjuctivitis and vernal keratoconjuctivititis. Clin Exp Allergy 1997; 27: 372–8.

First E et al. Dose standarization of botulinum toxin. Lancet Apr. 23, 1994; 343 (8904): 1035.

Hayashi N et al. Giant cell angiofibroma of the orbit and eyelid. Ophthalmology 6/99; 106(6): 1223–9.

Jensen W et al. The sesceptibility of the mallard duck (Anas platyrhynchos) to Clostridium botulinum c2 toxin. Jpn J Med Sci Biol 3/80; 33(2): 81–6.

Just I et al. ADP–ribosylation of Drosophilia indirect–flight–muscle actin and arthrin by clostridium botulinum C2 toxin and Clostridium perfringens iota toxin. Biochem J 4/93: 2391 (Pt 2): 409–12.

Kinde H et al. Clostridium botulinum type–C intoxication associated with consumption of procesed alfalfa hay cubes in horses. J Am Vet Med Assoc Sep. 15, 1991; 199(6): 742–6.

Lambiase A et al. Increase plasma levels of substance P in vernal keratoconjuctivitis. Invest Ophthalmol Vis Sci 9/97; 30(10): 2161–4.

Lambiase A et al. Expression of nerve growth factor receptors on the ocular surface in healthy subjects and during minifestation of inflammatory diseases. IOVS 6/98; 38(7): 1272–5.

Leon A et al. Mast cells synthesize, store, and release nerve growth factor. Proc Natl Acad Sci 4/94; 91; 3739–43.

Levi–Montalcini R et al. Update of the NGF saga. J Neurol Sci 1995; 130: 119–127.

Levi–Montalcini R et al. Nerve growth factor: from neurotrophin to neurokine. TINS 1996; 514–20.

Lewin G et al. Nerve Growth Factor and nociception. TINS 1993; 16(9): 353–9.

Matter K et al. Actin involvement in exocytosis form PC12 cells: studies on the influence of botulinum C2 toxin on stimulated noradreneline release. J Neurochem 2/89; 52(2) 370–6.

Mauss S et al. Inhibition of the contraction of the isolated longitudinal muscle of the guinea–pig ileum by botulinum C2 toxin: evidence for a role of G/F–actin transition in smooth muscle contraction. Naunyn Schmiedebergs arch Pharmacol 9/89; 340(3): 345–51.

Mendell L et al. Nuerptrophins, Nociceptors, and Pain. Microscopy Res. Technique 1999; 45;252–61.

Nakamura S et al. C2 toxin production by Clostridium botulinum type C strains producing no C1 toxin. Jpn J Med Sci Biol 4/79; 32(2): 128–9.

Nakamura S et al. Sporulation and C2 toxin production by Clostridium botulinum type C strains producing no C1 toxin. Microbial Immunol 12978; 591–6.

Ohishi I et al. Histopathological effect of botulinum C2 toxin on mouse intestines. Infect Immun 1/84; 43(1): 54–8.

Pardo F et al. Long–term follow–up of patients undergoing definitive radiation therapy for sebaceous carcinoma of the ocular adnexae. Int J Radiat Oncol Biol Phys Mar. 15, 1996; 34(5): 1189–90.

Pearce L et al. Pharmacolgic characterization of botulinum toxin for basic science and medicine. Toxicon 9/97; 35(9): 1373–412.

Pearce L et al. Botulinum toxin: death versus localized denervation. J R Soc Med 4/95; 88(4):239–40.

Pearce L et al. The median paralysis unit: a more pharmacologically relevant unit of biologic activity for botulinum toxin. Toxicon 2/95; 33(2): 217–24.

Pearce L et al. Measurement of botulinum toxin activtiy: evalutaion of the lethality assay. Toxicol appl Pharmacol 9/94; 128(1): 69–77.

Pearce L et al. Botulinum toxin ptency: a mystery resolved by the median paralysis. J R Soc Med 9/94; 87(9): 571–2.

Ritter A et al. Regulation of myelinated nocipeptor function by nerve growth factor in neonatal and adult rats. Br Res Bul 1993; 30: 245–49.

Sanico A et al. Nerve growth factor expression and release in allergic inflammatory disease of the upper airways. Am J Respir Crit Care Med 2000; 161: 1631–5.

Simpson L A comparison of the pharmacological properties of Clostridium botulinum type C1 and C2 toxins. J Pharmacol Exp Ther 1/82; 223(3): 695–701.

Simpson L Molecular basis for the pharmacological actions of Clostridium botulinum type C2 toxin. J Pharmacol Exp Ther 9/84; 230(3):665–9.

Tarsy D et al. Myasthenia gravis after botulinum toxin A for Meige syndrome. Mov Disord 7/00; 15(4): 736–8.

Troll G et al. Diplopia after cataract surgery using 4% lidocaine in the absensce of Wydase. J Clin Anesth 11/99; 11(7): 615–6.

Wex C et al. Effects of clostridium botulinum C2–inducted depolymerisation of actin on degranulation of suspended and attached mast cells.. Naunym–Schmiedeberg's Arch Pharmacol 1997; 355:319–27.

Woolf C et al. Peripheral cell types contributing the hyperalgesic action of nerve growht factor in inflammation. J Neurosci Apr. 15, 1996; 16(8): 2716–23.

Yamaji M et al. Role of substance P in experimental allergic conjunctivitits in guinea pigs. Meth Find Exp Clin Pharmacol 1997; 19(9):637–43.

* cited by examiner

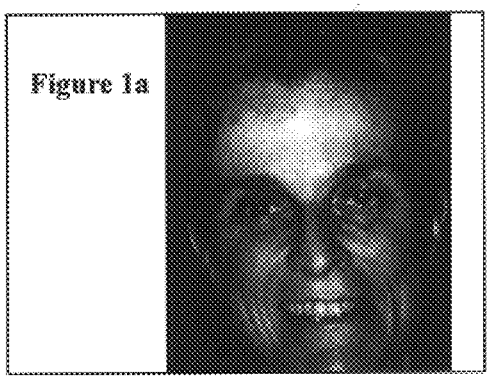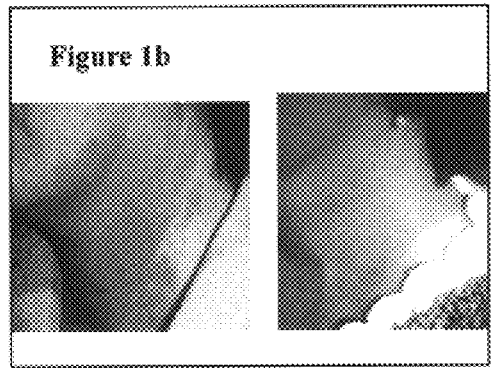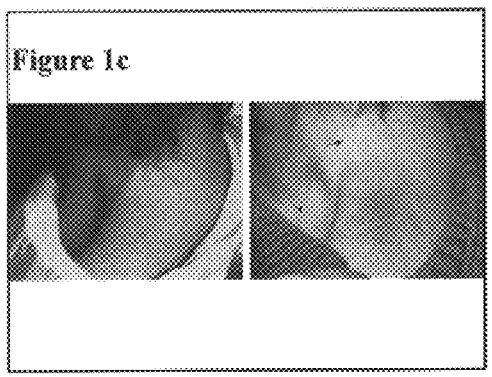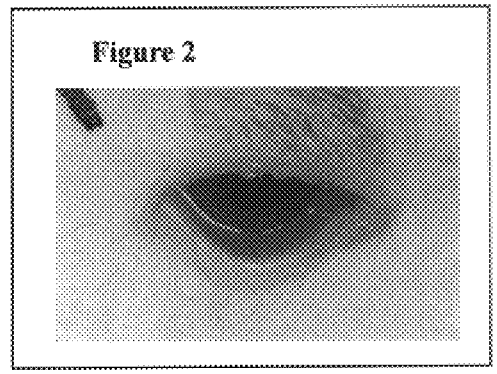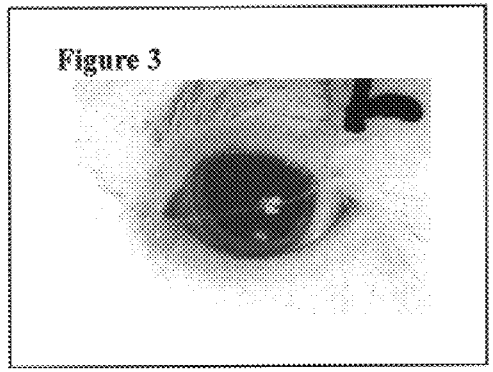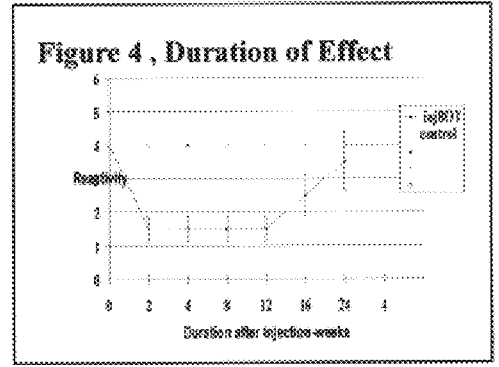

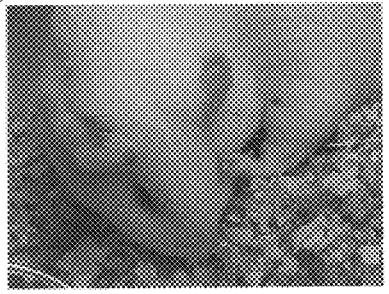
Figure 5 Discomfort Behavior
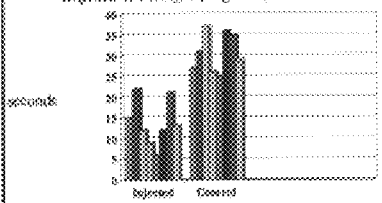
Figure 6

CYTOTOXIN (NON-NEUROTOXIN) FOR THE TREATMENT OF HUMAN HEADACHE DISORDERS AND INFLAMMATORY DISEASES

FIELD OF INVENTION

This invention relates to the composition of chemodenervating agents used for the treatment of diseases. The invention offers an improvement on the prior art by eliminating the muscle-weakening side effect of prior-art chemodenervating agents. This is achieved by eliminating the neurotoxin component of the chemodenervating agent.

BACKGROUND OF THE INVENTION

Migraine and tension headaches are a major cause of loss of productivity for those afflicted, usually due to pain and associated systemic symptoms. The syndrome of migraine and other essential headaches is characterized by severe throbbing headaches often made worse by physical activity and associated with aversion to light and sound. The syndrome often, but not always, includes nausea and/or sometimes vomiting as major components. The pain is often unilateral or localized to a portion of the head. The condition is episodic in nature, with episodes typically lasting 4–72 hours.

Tension headache is the most common type of essential headache and is characterized by head pain not associated with any structural lesions, often not associated with nausea, and occurring more frequently and less episodically than migraine headache.

Recently *botulinum* toxin injections within the head and neck region have been advocated as a method to treat migraine headache, tension headache, and myofascial pain, both acutely and for prophylaxis. Efficacy for both myofascial pain and migraine headaches has been shown in double-blind placebo-controlled trials. However, the mechanism of action has not been clearly explained, as *botulinum* toxin has been thought to exert its beneficial effects for most indications by causing decreased muscle tone and contractility. The major limiting factor involved in injecting *botulinum* toxin is the muscle-weakening effect. For instance, ptosis (drooping of the upper eyelid) is the major side effect caused by the injection of neurotoxin for the treatment of human headache disorders. This results from the neuromuscular paralytic effects of the neurotoxin component of the *botulinum* toxin molecule.

Recently, the present inventor has shown *botulinum* toxin to have anti-inflammatory components, both in vivo in man and in animal experiments. This unique property has not been previously appreciated or defined and in fact may explain the mechanism of action by which *botulinum* toxin exerts its beneficial effects in essential headache disorders (migraine and tension headaches) as well as in other medical conditions. Evidence that *botulinum* toxin acts on the inflammatory response associated with essential headaches can be categorized into clinical observations and animal experiments as disclosed herein.

BRIEF SUMMARY OF THE INVENTION

A limiting property of *botulinum* toxin for the treatment of pain or inflammatory disease relates to its weakening effect on muscle tissue caused by blocking acetylcholine release by its neurotoxin component. The utility of the invention described herein is based upon a compositional change to the *botulinum* exotoxin proteins used in medical practice that eliminates neurotoxin activity, while maintaining a biological activity that is capable of suppressing pain and inflammation. Such compositional improvement allows the exotoxin protein to be used without the attendant risk of inducing muscle atrophy and weakness, while retaining a biological effect useful for the clinical relief-of pain and discomfort.

DETAILED DESCRIPTION

*Botulinum* toxin exists as multiple immunotypes (A–G), which have been investigated as to specific medical properties. The immunotypes share little cross reactivity and have been shown to differ in chemical composition and biological behavior when injected at sublethal doses to produce a regional dose-dependent effect. Differences in biological activity between the various immunotypes include (1) differing durations of action at the injection site and (2) differing regional denervation potencies, measured as the relative quantity of LD 50 units required to produce a given regional or clinical effect.

*Botulinum* toxin application to human essential headache disorders was originally identified in myofascial tension type headaches (see Acquardro and Borodic, Treatment of myofascial pain with *botulinum* A toxin. Anesthesiology. 1994 Mar;80(3):705–6), and later, as a coincident finding, for migraine headache. The coincident finding and application for migraine was noted as *botulinum* toxin was being used as a neurotoxin to remove forehead wrinkles. Regional facial muscular weakening effaces facial and forehead dynamic lines associated with aging. Such dynamic lines are produced by facial muscle tone as forces are transmitted from facial muscles to dermal attachments of these muscles in facial skin. The neurotoxin component was thought active in the treatment of headaches and pain during this period. Prior art U.S. Pat. No. 5,714,468 teaches that the neurotoxin (that component of *botulinum* toxin which causes neuromuscular paralysis) is the active agent and mechanism by which *botulinum* toxin is effective for the treatment of migraine and other forms of pain.

Of the immunotypes of *botulinum* toxin, a mutant and unusual derivative subtype of *botulinum* toxin is *botulinum* toxin C2, which exhibits no neurotoxin properties. *Botulinum* toxin C2 possibly represents a mutated gene derivative which demonstrates no neurotoxin capability, yet is toxic by other cytopathic mechanisms (Ohishi, I. Response of mouse intestinal loop to *botulinum* C2 toxin: enterotoxic activity induced by cooperation of nonlinked protein components. Infect Immun 1983 May;40(2):691–5). The proteinaceous materials derived from *botulinum* C2 strains are, however, biologically active and have been demonstrated to cause lethal effects by mechanisms other than neuromuscular paralysis. The materials are described as cytotoxic in nature. Described herein is the demonstration of *botulinum* type C2 as a specific inhibitor of inflammation in a sensitized animal model, and reduction to practice utilizing *botulinum* C2 as a (1) therapy for inflammation and (2) therapy for migraine and tension headache treatment.

*Botulinum* toxin has been used for the past 16 years to treat various forms of facial movement disorders, including Blepharospasm, hemifacial spasm, bruxism, and synkinetic facial movements after chronic facial palsy. This substance has also proven substantial utility for the treatment of spasmodic torticollis, spasticity associated with cerebral palsy, stroke, occupational hand cramping, and speech disorders (spasmodic dysphonia). In each of these applications, the mechanism of action had been postulated to involve weakening of a fixed volume of muscle around the area injected for a period of 10–18 weeks, with complete reversal of the weakening effect after that time. During the period after the injection, the weakening is correlated to (1) blockage of release of acetylcholine from the presynaptic nerve terminal at the neuromuscular junction, (2) atrophy similar to motor nerve denervation atrophy in the area over which the toxin diffuses, (3) decreased contractility within the muscles over which the toxin diffuses, (4) motor nerve terminal sprouting from the motor axon terminal, (5) spread of acetylcholinesterase and acetylcholine receptors from the post synaptic membrane, and (6) reversibility of the above findings within the denervation field after 10–18 weeks.

Collectively the above describes a cycle that has been well characterized in the observations of Duchenne (Scott AB *Botulinum* toxin injection of eye muscles to correct strabismus. Trans Am Ophthalmol Soc 1981;79:734–70). Additionally, it has been well established that *botulinum* toxin has local effects on autonomic nerve ganglion and nerve function. (MacKenzie I, Burnstock G, Dolly JO The effects of purified *botulinum* neurotoxin type A on cholinergic, adrenergic and non-adrenergic, atropine-resistant autonomic neuromuscular transmission.Neuroscience 1982 Apr;7(4):997–1006).

The medical utility of *botulinum* toxin has been based primarily on the neuromuscular effects of *botulinum* neurotoxin, as the neurotoxin generates the cycle described in steps (1)–(6) above. The definition of a neurotoxin is an agent capable of producing death by action on a portion of the central or peripheral nervous system in such a manner as to destroy or critically impair organism function. In the case of *botulinum* neurotoxin, the action is at the level of the neuromuscular junction, leading to disseminated weakness with paralysis of critical muscles such as the muscles driving respiratory ventilation. The lethal effect, which occurs at a critical point of muscular weakness, is asphyxiation and suffocation. The pharmacological principle governing the utility of *botulinum* toxin in the treatment of human diseases is that a regional effect occurs at a diluted concentration-dose remote from the lethal concentration-dose. Stated another way, this principle is the property of neurotoxin that allows a regional effect at a neurotoxin dilution and concentration substantially lower than that concentration that would cause a lethal systemic effect for the various types of *botulinum* neurotoxin used. That lower concentration allows for regional muscular weakening, which has been thought to be the sole mechanism by which the neurotoxin exerts its beneficial action in diseases involving spastic or involuntary movement.

Despite this scientific understanding of *botulinum* toxin as a neurotoxin, there remains insufficient understanding of the biological tissue effects to explain observed utility for other medical conditions such as the treatment of human pain such as occurs in essential headache disorders, myofascial pain, and certain pain components associated with dystonias. Also, there exists no explanation of the mechanism by which *botulinum* toxin is effective in reducing inflammation within the denervation field. The action of *botulinum* toxin as a neurotoxin, a substance acting at the neuromuscular junction causing muscular weakness, fails to provide a sufficient basis for the mechanism by which utility is achieved for conditions which are not associated with abnormality in movements.

Described herein is the bioeffect thought critical to the property of *botulinum* toxin that is directly or indirectly related to its ability to relieve human pain. Also described are methods by which this property can be chemically dissociated from the neurotoxin component (muscle-weakening component) of the *botulinum* toxin pharmaceutical agent, thereby generating a new perfected *botulinum*-derived pharmaceutical agent capable of eliminating the undesirable muscle weakness associated with injection of prior-art *botulinum* toxin preparations into a diseased area.

Efforts to explain the critical property of *botulinum* toxin capable of causing an improvement in pain associated with essential headache disorders and migraine headaches initially came from observations of the patient seen in FIG. 1. This 53 year old woman experienced flushed face and disseminated itching following physical exertion. The face demonstrated hives, associated with the flushing. Her past medical history was significant for Bell's palsy for which she received a *botulinum* type A injection for the treatment of forehead asymmetry. It was noted that after the *botulinum* toxin was injected into the forehead, there would be white blotches appearing on the forehead in which there was no flushing, and no hive formation (blocked urticaria within the denervation field). (See FIG. 1). This patient exhibited this effect after physical exertion consistently for a period of three months after the *botulinum* type A injections and the effect slowly faded thereafter. This duration of effect is typical for *botulinum* type A injections.

The syndrome of cholinergic urticaria is typically associated with urticarial eruption after exertion. Sometimes the condition is also associated with symptoms of asthma. The pathophysiology has been linked to increased release of circulating histamine, as well as mast cell degranulation. As the above-noted bioeffect appeared novel and not well explained by existing understanding of *botulinum* toxin efficacy, efforts were made to confirm the effect on human mast cells in an in vivo laboratory experiment. A Hart Bartley guinea pig (a guinea pig prone to type 1 hypersensitivity reactions) was sensitized to pollen spores (short ragweed pollen-Ambrosia artemisfolia), with aerosolized spores sprayed into the conjunctiva of the animals for a period of two weeks. Prior to this exposure, the animals had no reaction to the pollen, with the conjunctival membranes appearing white and quiet after exposure. After two weeks however, animals were again exposed to the short ragweed pollen, which caused acute edema, erythema, itching, flame hemorrhages within the conjunctiva, and distortion of the eyelids. This animal model has been pathologically characterized as being associated with measurable mast cell degranulation histologically, when pollen spores were exposed to sensitized conjunctiva.

The typical reaction is seen in FIG. 2. FIG. 3 shows the protection by *botulinum* toxin from the inflammatory response after exposure to the short ragweed pollen. The duration of the protective effect is demonstrated in FIG. 4 for a series of 6 animals followed for 6 months. Given the demonstrated efficacy in cholinergic urticaria and demonstrated anti-inflammatory effect in the allergic animal model measuring immediate hypersensitivity reactions, reactions thought to represent mast cell degranulation phenomenon, it appears that *botulinum* toxin either directly or indirectly is influencing the system which involves mast cells, histamine, possibly serotonin, and other related autocoids in such a fashion to cause a blocked physiological response important to the pathogenesis of certain forms of inflammation and pain. Due to release of autocoids, such as various forms of prostaglandins and leukotrienes as well as other formed and generated local mediators, and as an obvious clinical observation, it is expected that the inflammatory response will be associated with pain degeneration by mechanisms relating to alterations of mast cell secretion or degranulation.

In a known physiological assay, the relationship between mast cell degranulation and pain is clearly demonstrated. After a type 1 hypersensitivity response is demonstrated on the forearm of a person with known allergy to an introduced allergen, there appears to be a typical wheal and flare response associated with the sensory perception of itching. This is known as the immediate response. After a period of 6–8 hours, a late response is occasionally noted, characterized not by itching but rather tenderness and pain. The immediate response is thought to be associated and effected by preformed mediators such as histamine, whereas the late response is thought to be associated with the leukotrienes and prostaglandins. The prostaglandins and leukotrienes are important in the late phase reaction and are associated with pain generation. Compounds known to block prostaglandin derivatives such as indomethacin and corticosteroids will also block the late phase reactions associated with mast cell degranulation. In cellular systems, dependent on the adhesion of mast cells, there has been observed an increase or decrease in secretion induced by C. botulinum C2 toxin. In suspended mast cells, pretreatment with botulinum C2 toxin causes inhibition of secretion. In contrast, in adherent mast cells, the destruction of the cytoskeleton by botulinum C2 toxin causes increase in secretion. Thus, the signaling is largely effected by adhesion of mast cells in cellular in vitro studies, and mast cells have the capability of being influenced by the non-neurotoxin botulinum C2.

There exists a relationship between mast cell activity and migraine and other forms of essential headaches. The pathophysiolgy of essential headaches and migraine has been thought to relate to mast cell function and mast cells degranulation. (Theoharides, TC. The mast cell: a neuroimmunoendocrine master player. Int J Tissue React 1996;1 8(1):1–21; Moskowitz, Ma. Neurogenic inflammation in the pathophysiology and treatment of migraine. Neurology 1993 Jun;43(6 Suppl 3):S 16–20; Delepine, L., Aubineau, P. Plasma protein extravasation induced in the rat dura mater by stimulation of the parasympathetic sphenopalatine ganglion. Exp Neurol 1997 Oct;147(2):389–400.)

Authors cited above have found that a relationship exists between mast cells and the possible mechanism by which pain is generated in headache disorders, postulating that mast cells play a functional role in the generation of pain nerve adaptation at C-fibers. Although postulated, it appears that no absolute proof relating mast cells to pain generation has been totally established.

Clinical observations have also linked allergy and mast cell function to the syndrome of migraine headache. The following factors indicate the relationship between mast cells and migraine based on the relationship between type I hypersensitivity reactions and migraine. (1) Hayfever allergy season brings out migraines. (2) Stress can be associated with both migraine and urticarial reactions. (3) Patients born to mothers with common migraine are more likely to have offspring with allergic asthma, a mast cell related disease. (4) A known migraine patient receiving a forehead bee sting experienced violent migraine headache within two minutes of the sting. (5) Forms of food allergy are thought to precipitate migraine headaches. (6) Components of headaches (light sensitivity) can also be associated with migraine. (7) Patients with migraine often have elevated blood histamine levels. (8) Mast cells are responsive to cytotoxins.

In each case, mast-cell-generated inflammation is conceived as a form of inflammation and/or tissue change that provokes genetically predisposed individuals to develop a violent painful sensory experience. Described herein is a cytotoxic botulinum-derived compound capable of blocking inflammation without causing a neurotoxic (neuromuscular) effect.

There exist both advantages and limitations of botulinum neurotoxins in the treatment of human essential headache disorders and human inflammation. Botulinum toxin has many advantages over existing therapy for the treatment of essential headache disorders. These include (1) lack of systemic side effects, particularly compared to the krypton class of drugs, (2) long duration of action (3–5 months), (3) maintenance free therapy (no pills, no autoinjections), (4) high degree of efficacy.

The major limiting factor is that the prior-art medication produces weakness. In a series of 104 patients treated with type A botulinum neurotoxin, the major side effect was ptosis from diffusion of the botulinum toxin into the orbital space (Borodic). Diffusion of botulinum toxin and attendant weakening effect is not seen only with the treatment of human pain syndromes, but also has been noted with treatment of movement diseases (blepharospasm) causing drooping lids (ptosis), and treatment of cervical dystonia (torticollis) causing difficulty swallowing food (dysphagia).

Hence for the treatment of movement disease the neurotoxin and weakening bioeffects of botulinum toxin are both helpful and a cause of complication. In diseases in which there is no involuntary muscular movements or tone, such as tension or migraine headaches, or forms of human inflammation, the neurotoxin effect would be more detrimental to human clinical applications, causing weakness solely as a complication. Here lies the fundamental utility of the present invention. Botulinum toxin exists as immunotypes A–G. Each immunotype is a neurotoxin and causes neuromuscular blockade and weakness when locally injected. However one strain of botulinum toxin, perhaps a mutant or derivative strain, has produced a non-neurotoxin protein which demonstrates a selective interaction with the mast cell, does not interact with the neuromuscular junction (neurotoxin), and does not produce weakness (as shown in FIG. 5). This botulinum protein is biologically active and theorized to act at important tissue sites relative to human pain, migraine headaches, tension headaches, and headaches involving human inflammation-involving mast cells, or mast-cell-contained mediators of inflammation.

This protein is characterized by those skilled in botulinum toxin technology as a cyotoxin, which causes intestinal inflammation as a cause of toxicity, without inducing muscular weakness. Clostridium botulinum C2 toxin, Clostridium perfringens iota toxin, and Clostridium spiroforme toxin act on ADP-ribosylate actin monomers. Toxin-induced ADP-ribosylation disturbs the cellular equilibrium between monomeric and polymeric actin and traps monomeric actin in its unpolymerized form, thereby depolymerizing actin filaments and destroying the intracellular microfilament network (intracellular actin cytoskeleton). Furthermore, the toxins ADP-ribosylate gelsolin actin complexes. These cytoskeletal modifications may contribute to the cytopathic action of this toxins.

The botulinum toxin used to practice the present invention may be prepared as follows. A preparation is made consisting of a Clostridium botulinum strain which produces solely C2 cytotoxin. Culture is accomplished with appropriate agents to procure the maximum number of LD 50 units per ml of culture solution. LD 50 units are determined using the mouse bioassay, and the preparation may be freeze-dried for the purpose of preservation and stability. A known quantity of bioactivity as determined by LD 50 is injected into the area in which pain, headache, or inflammation have been diagnosed by the clinician. A quantity for injection is chosen by the clinician based on LD 50 units.

Botulinum C2 is characterized as a non-neurotoxin, capable of causing increased vascular permeability, fluid accummulation in ligated intestine, and rounding of tissue cultured cells. Bioassay for the activity can be accomplished by a "time to mouse death method" after intravenous infusion, or by intraperitoneal injection. Anti-neurotoxin sera to botulinum toxin may be used to confirm complete neutralization of the neurotoxin prior to bioassay. Preparation may be accomplished by biochemical isolation from spent cultures, or by recombinant production using either E coli or a Clostridium expression system, given that genes encoding the C2 protein have been elucidated.

Botulinum C2 cytotoxin has been shown to consist of two protein components not covalently bound, segment I and segment II, both required for the biological activity of the toxin. The following represents examples of preparations that can be used to isolate the C2 property from neurotoxin properties of botulinum toxin. Because the biological activity of component II has not been recovered after freeze-drying, a liquid formulation of the material would be preferred.

Following is a detailed description of an example method for isolating botulinum toxin C2.

1. Inoculum medium. Prepare 250 mls/carboy of media containing 2% trypticase peptone, 1% protease peptone, 1% yeast extract, 1.0% glucose and 0.1% cysteine HCI, ph 7.4.
2. Incoculation with type C stock. Inoculate each flask with 0.5 ml of thawed working stock culture of C botulinum type C. Incubate for 24 hours.
3. Production medium. Prepared 9.5 L carboy of media containing 2% trypticase peptone, 1% protease peptone, 1% yeast extract, 1.0% glucose (prepared and autoclaved separately in 400 ml of distilled water) and 0.1% cysteine HCl, pH 7.4.
4. Inoculate production medium. Add glucose solution and 250 ml of inoculum to each 9.5 L carboy. Incubate at 30 degrees C for 6 days.
5. Harvest toxin. Toxin was harvested by addition of 2 g/L RNA and dropping the pH to 3.4 by addition of 3 N sulfuric acid. Toxin is allowed to settle for at least 16 hours and then collected by centrifugation.
6. Wash toxin. Toxin is washed with 1 liter of distilled water and allowed to settle. Washed toxin is collected by centrifugation (10K rpm for 10 min at 10 degrees C) and the toxin is extracted from the pellets.
7. Na phosphate extraction of the toxin. Thoroughly suspend the toxin pellets in 600 ml of 0.2 M Na Phosphate buffer+0.5 M NaCl, pH 7.0, and extract at room temperature for 2 hours. The extract is centrifuged and the new extraction repeated on pelleted material with an additional 400 ml of the same buffer for 2 hours.
8. Ammonium sulfate precipitation. Precipitation of the extract by the addition of ammonium sulfate (39 g/100 ml).
9. Prepare toxin for chromatography. Collect the precipitate by centrifugation at 8000 rpm for 10 min. Dissolve the precipitate in 50 nM of sodium citrate, pH 5.5, using as small volume as possible.
10. Dialysis of toxin solution. Toxin solution is dialyzed against 3 X changes in citrate buffer overnight at 4 degree C. and centrifugation ensues.
11. DEAE-Sephadex A-50 chromatography. Centrifuged material is chromatographed at room temperature on a -1 DEAE sephadex A-50 column (5 cm×50 cm, Sigma Chemical Co., St Louis , Mo.) equilibrated with the same buffer. One tenth of the column volume or less is chromatographed in a single passage with the toxin complex eluting in the first column without a gradient. Fractions from the protein peak which have a 260/278 absorbance ratio of less than 0.70 are pooled. The material must have a specific toxicity of>10 (6) LD 50/mg. Pooled toxin is precipitated with 60% ammonium sulfate.
12. Separation of Component I and II may be accomplished with further chromatographic separation to achieve further purification.

The Swiss Webster mouse bioassay for lethality of the purified preparation is utilized to quantify bioactivity. Anti-neurotoxin antibody is used for characterization to insure lethal bioeffects in the animal bioassay are explicitly not the result of paralysis induced by neurotoxin.

Characterization of the preparation prior to dilution is accomplished with gel electrophoresis, nucleic acid content assay, specific activity assay, and protein content assay for purity and consistency. Dilution accompanied by ultrafiltration establishes sterility. A region is targeted by the physician intending to treat a body region afflicted with the inflammatory process. A known selected bioactivity measured in LD 50 units is injected into the region. After 10 days, the region is inspected for the cardinal signs of inflammation. Booster doses may be given if necessary.

DETAILED DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 1a. Note the white blotches on the patients forehead indicating blocked urticaria formation within the denervation field. The patient suffers from typical cholinergic urticaria. The blocked area of urticaria, which includes edema, erythema, and altered sensation corresponds to the usual diffusion field of botulinum toxin at doses between 5–20 LD 50 units.

FIG. 1b. Note the pattern of erythema on the neck of this patient with dystonia and pain. The picture has been digitally enhanced to emphasize the erythema. Note that in this patient both the erythema and the pain was improved within the denervation field surrounding the injection (arrow).

FIG. 1c. Note the pattern of erythema on the neck of this patient with cervcial dystonia. This patient has been well documented to exhibit circulating neutralizing antibodies to the neuromuscular paralyzing effects of the immunotype A Clostridium botulinum toxin. No muscular atrophy is seen in injected muscle yet there is a block in the erythema surrounding the injection site in a dimension equivalent to the diffusion potential for 20–40 LD 50 units of botulinum toxin. As neutralizing antibodies to the neuromuscular effect of botulinum did not block this anti-pain and anti-inflammatory effect, the anti-inflammatory effect may be the result of a different immuno-reactive epitope on the botulinum toxin proteins.

FIG. 2. 15 minutes after short ragweed pollen spores were exposed to the sensitized animal. Note the red eye, edema and distortion of the lower eyelid position.

FIG. 3. Botulinum toxins type A, type C, and type C2, when injected, protect against the inflammatory effects associated with hypersensitivity to short ragweed pollen, hence demonstrating the anti-inflammatory effects of botulinum toxin in the animals' orbit tissues.

FIG. 4. The duration of anti-inflammatory effects in a series of six animals followed for 6 months.

FIG. 5. Behavior reaction to irritable stimuli created by ragweed pollen in sensitized Guinea pig conjunctiva. Rubbing the inflamed irritated eye is quantified over a period of 15 minutes after exposure to the pollen.

FIG. 6. The sensitized Guinea pig conjunctiva is injected with *botulinum* C2 preparation. The irritation quantified by rubbing behavior is diminished significantly (P<0.05, n=6).

What is claimed is:

1. A pharmaceutical composition for treatment of inflammation or pain comprising purified protein, wherein said purified protein is derived from *Clostridium botulinum*, and wherein said purified protein exhibits no neurotoxin properties.

2. The pharmaceutical composition of claim 1, wherein said purified protein is derived from *Clostridium botulinum* type C.

3. The pharmaceutical composition of claim 1, wherein said purified protein comprises *botulinum* toxin C2.

4. The pharmaceutical composition of claim 3, wherein said *botulinum* toxin C2 is purified from a bacterial strain expressing at least one cloned gene encoding a protein component of said *botulinum* toxin C2.

5. A method for treatment of inflammation or pain comprising,
administering locally a therapeutically effective amount of a pharmaceutical composition,
wherein said pharmaceutical composition comprises a purified protein derived from *Clostridium botulinum*,
wherein said purified protein exhibits no neurotoxin properties, and
wherein said administration is for a time and under conditions sufficient to reduce the inflammation or pain.

6. The method of claim 5, wherein said administration of said pharmaceutical composition produces no muscular weakening.

7. The method of claim 5, wherein said therapeutic effect is mediated by inhibition of secretion of autocoids from mast cells, without antagonizing neuromuscular transmission.

8. The method of claim 5, wherein said purified protein is derived from *Clostridium botulinum* type C.

9. The method of claim 5, wherein said purified protein comprises *botulinum* toxin C2.

10. The method of claim 9, wherein said *botulinum* toxin C2 is purified from a bacterial strain expressing at least one cloned gene encoding a protein component of said *botulinum* toxin C2.

11. The method of claim 5, wherein said administration is by injection.

12. The method of claim 5, wherein said administration is by topical application.

13. The method of claim 5, wherein said administration is of a dose of from approximately 5 to approximately 20 LD 50 units, as measured using the Swiss Webster mouse bioassay.

14. The method of claim 5, wherein said administration is of a dose of from approximately 20 to approximately 40 LD 50 units, as measured using the Swiss Webster mouse bioassay.

15. The method of claim 5, wherein the inflammation or pain is caused by a disorder selected from the group consisting of tension headache, migraine headache, postoperative head and neck pain, trigeminal neuralgia, temporal mandibular joint syndrome, and essential headache.

16. The method of claim 15, wherein said local administration is to the head.

17. The method of claim 15, wherein said local administration is to the neck.

18. The method of claim 5, wherein the inflammation or pain is regional muscle pain or inflammation.

19. The method of claim 5, wherein the inflammation or pain comprises symptoms selected from the group consisting of inflammation, pain, edema, redness, and itching.

20. The method of claim 5, wherein the inflammation or pain is caused by a disorder selected from the group consisting of asthma, eczema, hay fever, excessive salivation, tearing, otitis, anal fissures, and cystitis.

21. The method of claim 5, wherein the inflammation or pain is caused by a disorder selected from the group consisting of gastrointestinal ulceration and gastric, small, and large intestinal inflammation.

22. The method of claim 5, wherein the inflammation or pain is caused by a disorder selected from the group consisting of myofascial pain, regional dystonia, spasmodic torticollis, blepharospasm, and hemifacial spasm.

23. The method of claim 5, wherein the inflammation or pain is caused by rheumatoid arthritis.

24. The method of claim 5, wherein the inflammation or pain is caused by vasculitis.

25. The method of claim 1, wherein said purified protein is prepared by biochemical separation to remove all neurotoxin properties.

26. The method of claim 5, wherein the inflammation or pain is caused by a disorder selected from the group consisting of allergic conjunctivitis and allergic blepharoconjunctivitis.

27. The pharmaceutical composition of claim 1, wherein said composition exhibits no muscle weakening properties.

28. The pharmaceutical composition of claim 1, wherein said composition is effective in treating conjunctivitis.

29. The pharmaceutical composition of claim 1, wherein said composition is effective in treating allergic conjunctivitis.

* * * * *